United States Patent
Beer et al.

(10) Patent No.: US 7,559,137 B2
(45) Date of Patent: Jul. 14, 2009

(54) METHOD FOR PROVIDING ELECTRICALLY CONDUCTIVE PATHS IN POLYMER TUBING

(75) Inventors: Lawrence P. Beer, Vienna, VA (US); Michael Adelstein, Odenton, MD (US); C. Paul Christensen, Tracys Landing, MD (US)

(73) Assignee: Potomac Photonics, Inc., Lanham, MD (US)

( * ) Notice: Subject to any disclaimer, the term of this patent is extended or adjusted under 35 U.S.C. 154(b) by 429 days.

(21) Appl. No.: 11/487,387

(22) Filed: Jul. 17, 2006

(65) Prior Publication Data

US 2008/0125754 A1    May 29, 2008

(51) Int. Cl.
*H01R 43/00* (2006.01)
*B32B 15/00* (2006.01)

(52) U.S. Cl. .............................. 29/825; 29/846; 29/847; 428/209

(58) Field of Classification Search .................. 29/825, 29/846, 847; 428/209
See application file for complete search history.

(56) References Cited

U.S. PATENT DOCUMENTS

| | | | |
|---|---|---|---|
| 4,469,843 A | 9/1984 | Lordi | |
| 5,006,119 A | 4/1991 | Acker et al. | |
| 5,024,232 A | 6/1991 | Smid et al. | |
| 5,084,022 A | 1/1992 | Claude | |
| 5,084,311 A * | 1/1992 | Liu et al. | 428/35.8 |
| 5,177,170 A | 1/1993 | Sarpeshkar et al. | |
| 5,203,777 A | 4/1993 | Lee | |
| 5,256,158 A | 10/1993 | Tolkoff et al. | |
| 5,344,419 A | 9/1994 | Spears | |
| 5,429,617 A | 7/1995 | Hammersmark et al. | |
| 5,435,889 A | 7/1995 | Dietrich | |
| 5,558,789 A | 9/1996 | Singh | |
| 5,738,683 A | 4/1998 | Osypka | |
| 5,843,172 A | 12/1998 | Yan | |
| 5,882,722 A | 3/1999 | Kydd | |
| 5,902,266 A | 5/1999 | Leone et al. | |
| 6,032,061 A | 2/2000 | Koblish | |
| 6,036,889 A | 3/2000 | Kydd | |
| 6,107,004 A | 8/2000 | Donadio, III | |
| 6,143,356 A | 11/2000 | Jablonski | |
| 6,287,628 B1 | 9/2001 | Hossainy et al. | |
| 6,379,745 B1 | 4/2002 | Kydd et al. | |
| 6,395,326 B1 | 5/2002 | Castro et al. | |
| 6,471,881 B1 | 10/2002 | Chai et al. | |
| 6,488,654 B2 | 12/2002 | Gonzalez et al. | |
| 6,503,574 B1 | 1/2003 | Skelly et al. | |
| 6,517,888 B1 | 2/2003 | Weber | |
| 6,558,733 B1 | 5/2003 | Hossainy et al. | |

(Continued)

*Primary Examiner*—C. J Arbes
(74) *Attorney, Agent, or Firm*—Rosenberg, Klein & Lee

(57) ABSTRACT

A method for forming electrically conductive patterns to provide an electrically conductive path on a polymer tube is provided. The method includes the steps of establishing a polymer tube and mounting such in a displaceable and rotatable mounting that is adapted to provide both axial and rotational motion. This is followed by forming at least one channel having a predetermined pattern in the polymer tube with a focused energy beam, the channel then being filled with an electrically conductive paste or electrically conductive slurry material. The polymer tube is then heated to temperatures less than 250° C. to cure the electrically conductive paste or electrically conductive slurry material. The electrically conductive paste or electrically conductive slurry material is then covered with a polymer layer.

13 Claims, 3 Drawing Sheets

U.S. PATENT DOCUMENTS

| | | |
|---|---|---|
| 6,616,651 B1 | 9/2003 | Stevens |
| 6,726,829 B2 | 4/2004 | Trozera |
| 6,757,970 B1 * | 7/2004 | Kuzma et al. .................. 29/847 |
| 6,872,204 B2 | 3/2005 | Houser |
| 6,970,734 B2 | 11/2005 | Eidenschink et al. |
| 2003/0062126 A1 | 4/2003 | Scaggs |
| 2004/0086674 A1 | 5/2004 | Holman |
| 2004/0167496 A1 | 8/2004 | Poole et al. |
| 2004/0193139 A1 | 9/2004 | Armstrong et al. |
| 2005/0085895 A1 | 4/2005 | Brown et al. |

* cited by examiner

METHOD FOR PROVIDING ELECTRICALLY CONDUCTIVE PATHS IN POLYMER TUBING

BACKGROUND OF THE INVENTION

1. Field of the Invention

The subject invention relates to a polymer tube with embedded electrical conductors, such as a medical catheter, adapted to be coupled with one or more electrical devices. Polymer tubes, such as catheters, are used in a variety of medical procedures. Embedded electrical conductors and electrically conductive sections are needed in several types of plastic catheters, such as those carrying electrical sensors or sensing electrodes. Conductor patterns of this type are used to transmit electrical signals along the length of the catheter and to connect sensors at ends of the catheter to electrical power and communication circuitry. These same conductor patterns may also exhibit radio-opacity and enhance diagnostic imaging of regions of the catheter in which they are embedded.

This invention is directed to medical apparatuses included catheters. This invention is further directed to systems and methods for electrically coupling sensors and other electrical equipment by embedding electrical conductors in the connecting catheter. Still further, this invention is related to catheters having electrically conductive leads embedded therein using laser applications.

2. Prior Art

Polymer tubes (such as catheters) for use in medical procedures are well-known in the art. Additionally, to enhance the fluoroscopic visibility of regions of a polymer tube (such as a catheter), marker rings fabricated from solid radio-opaque material such as platinum, gold, tungsten or palladium are frequently applied to the outside of the catheter by swaging or other bonding means. Many of these metallic radio-opaque materials are electrically conductive. Marker rings of this type, however, are typically limited to cylindrical geometry and have limited utility for transmitting and routing electrical signals. They are also subject to detachment during use of the catheter and also produce undesirable features on a polymer tube surface, such as bumps and indentations.

As medical procedures evolve to utilize catheter delivery of increasingly complex sensors and actuators to various locations within the body, there is a need to incorporate increasingly complex conductor networks within the catheter device (polymer tube). These conductor networks frequently are required to have complex geometries, and carry high-frequency or large amplitude signals while maintaining minimal impact on the mechanical and biochemical properties of the plastic catheter. These often-conflicting requirements can be met when it is possible to produce small, highly conductive elements within the polymer tube (catheter) wall with only minimal limitations on their geometric configuration.

The best prior art known to Applicant includes U.S. Pat. Nos. 6,488,654; 4,469,843; 6,032,061, 6,616,651; 5,006,119; 6,872,204; 6,032,061; 5,738,683 and U.S. Patent Application Publications 2004/0167496; 2004/0106913.

Prior art systems such as that shown in U.S. Pat. No. 6,488,654 direct themselves to utilizing lasers or other cutting tools to remove material from a localized section of a catheter wall. Such systems do not provide filling of the channels with any type of electrically conductive material.

Prior art systems such as that shown in U.S. Pat. No. 4,469,843 direct themselves to using radio-opaque material mixed with polymeric material to fabricate sections of a catheter tubing to provide fluoroscopic marking. As detailed above, marker rings of this type are typically limited to cylindrical geometry and have limited utility for transmitting and routing electrical signals.

Prior art systems such as that shown in U.S. Pat. No. 6,032,061 direct themselves to the fabrication of an electrophysiology catheter incorporating several electrically conductive wires enclosed in the hollow center portion of a catheter. Embedding wires in the tube walls to improve the mechanical strength of plastic catheters is also well-known in the prior art. Using wires in the lumen takes away functionally from a polymer tube by occupying the hollow center portion.

Prior art systems such as that shown in U.S. Pat. No. 6,616,651 and references therein direct themselves to techniques for embedding spirally wound wires into the walls of plastic catheter tubing. Such systems as shown in U.S. Pat. Nos. 6,032,061 and 6,616,651 might be capable of carrying electrical signals, although the technique is not well suited to fabrication of complex electrical circuitry in which multiple signals must travel to and from electrical devices mounted in or on a catheter (a polymer tube). Furthermore, the use of wires within a catheter can be hazardous as such catheters and polymer tubes are used in medical procedures. Minimizing the parts, such as extraneous wires that are electrically conductive, while enhancing functionality of a polymer tube by enabling complex electrical configurations is a need that is yet to be fulfilled in the art.

None of the prior art provides for a combination of steps as herein presented comprising a method for forming electrically conductive patterns to provide an electrically conductive path on polymer tubing which allows for a maximum of efficiency and cost effectiveness with a minimum of defects.

SUMMARY OF THE INVENTION

The present invention provides for a method for forming electrically conductive patterns to provide an electrically conductive path on a polymer tube. The method includes the steps of establishing a polymer tube and mounting the polymer tube in a displaceable and rotatable mounting that is adapted to provide both axial and rotational motion. A focused energy beam is then used to form at least one channel having a predetermined pattern in the polymer tube, the channel then being filled with an electrically conductive paste or electrically conductive slurry material. The polymer tube is then heated to temperatures less than 250° C. to cure the electrically conductive paste or electrically conductive slurry material. The electrically conductive paste or electrically conductive slurry material is then covered with a polymer material.

It is a principal objective of the subject device and method of forming electrically conductive paths in a polymer tube to provide an efficient process for creating electrically conductive patterns on a polymer tube.

It is another object of the present invention to provide a polymer tube with electrically conductive paths, the type of which can be used in medical procedures, that can be coupled to one or more electrical device.

It is yet another object of the present invention to provide increasingly complex networks within a polymer tube such as a catheter while maintaining minimal impact on the mechanical and biochemical properties of the catheter.

DESCRIPTION OF THE PREFERRED EMBODIMENTS

Referring to FIGS. 1-7, there is shown an electrically conductive polymer tube 2 that is coupled to electrical devices and a method for forming electrically conductive patterns to provide an electrically conductive path on the polymer tube 2. The polymer tube 2 may be any type of well-known type of polymer tube 2, such as, a catheter. Preferably, the polymer tube 2 is of the type used in medical procedures, specifically for use within the human body.

The polymer tube 2 is adapted to be coupled to electrical devices. There are many instances during medical procedures that devices requiring electrical energy are used. One example of an electrical device is a video camera. Supplying power to a video camera through a polymer tube with electrically conductive paths, 2, such as a catheter, minimizes the need for various devices that are electrically conductive by incorporating as much into the polymer tube 2. The polymer tube 2 has a proximal end 4 and a distal end 6. One of either the proximal or distal end 4, 6 will couple to an electrical source while the other will couple to the electrical device. In this manner, the use of the polymer tube, such as a catheter, is functionally increased.

Figure 1:
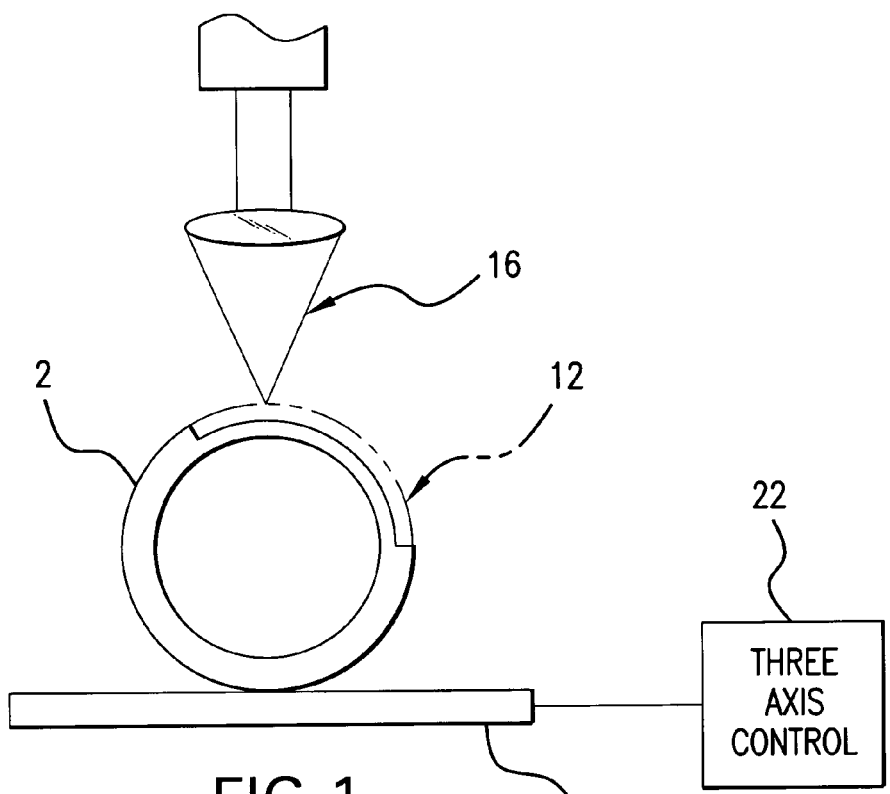
FIG. 1 is a cross-sectional view of the system for forming electrically conductive patterns on a polymer tube.
Figure 2:
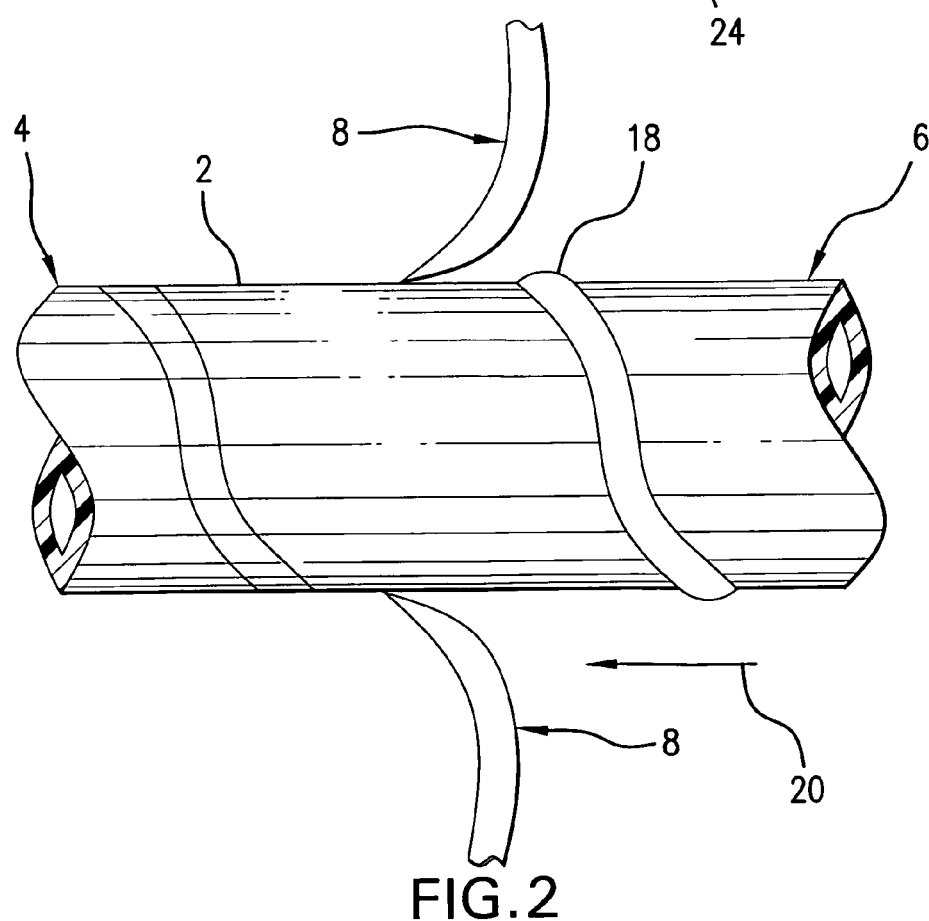
FIG. 2 is a perspective view of the polymer tube subsequent to the step of filling the channels having a predetermined pattern.

Referring to FIGS. 1-2, there is shown a method for forming electrically conductive patterns to provide an electrically conductive path on a polymer tube 2. Initially, a polymer tube 2 is established with the polymer tube 2 having an axis defining an axial direction 20. As detailed above, the polymer tube 2, may for example, be a well-known catheter and includes a proximal end 4 and a distal end 6. Preferably, the polymer tube 2 is of the type used in medical procedures.

The polymer tube 2 is then mounted in a displaceable and rotatable mounting 24 (shown schematically) which is controlled by control electronics 22 to provide displacement about three axes. Mounting 24 may be any one of a number of commercially purchasable displacement control systems well known in the art that is adapted to provide both axial and rotational motion. The mounting could be, for example, a high-speed motion system that provides both axial and rotational motion. The displaceable and rotatable mounting facilitates rapid access of a focused energy beam 16 to all portions of the polymer tube 2. Additionally, the displaceable and rotatable mounting enhances proper formation of various predetermined patterns of the channels 12 (as will be detailed in following paragraphs).

In this manner, the displaceable and rotatable mounting ensures access to the entirety of the polymer tube 2 by the focused energy beam 16. Such is important to ensure proper formation in terms of depth and pattern of the channel(s) 12 in the polymer tube 2.

Once the polymer tube 2 is mounted in the displaceable and rotatable mounting, at least one channel 12 having a predetermined pattern is formed in the polymer tube 2. The channel 12 is formed in the polymer tube 2 with a focused energy beam 16, as shown in FIG. 1. The focused energy beam 16 may be a laser, a source of non-coherent light, an electron beam generator, or any other suitable means for generating energy that can be translated into a focused energy beam 16.

In the preferred embodiment, the focused energy beam 16 is a diode-pumped, solid-state neodymium laser, such as a neodymium vanadate laser. In order to effectively form the channel 12 (by ablation) on the surface of the polymer tube 2, it is preferred that the output of the focused energy beam 16 be frequency-tripled or frequency-quadrupled in order to produce wavelengths shorter than 360 nm. The focused energy beam 16 is used for the ablation of at least one channel 12 and further forms the predetermined patterns of the channel 12 in the polymer tube 2.

Operation of the focused energy beam 16, such as a laser, at power levels high enough to produce ablation or vaporization of the polymer material while the focused energy beam 16 is rapidly scanned across the surface of the polymer tube 2 provides a means for fabrication of patterns of channels that are specific in terms of depth and contour in the polymer tube 2. For example, each laser pulse removes a layer of material of less than a few microns thickness from the illuminated region of the polymer tube 2. The depth and shape of ablated channel 12 may thereby be defined by controlling the number of pulses delivered to each illuminated region as the focus energy beam 16 is scanned over the channel 12.

The computer control is in electrical communication with the laser forming the focused energy beam 16 and the displaceable and rotatable mounting 24. The control 22 may be either set automatically, for creating a set of desired paths, or the system may be operated manually.

Referring to FIG. 1, the focused energy beam 16 creates at least one channel 12 in the polymer tube 2. As detailed above, mounting the polymer tube 2 in the displaceable and rotatable mounting enables the focused energy beam 16, which may be stationary or alternatively displaceable, to access the entire polymer tube 2 thereby forming at least one channel 12 therein.

Figure 5:
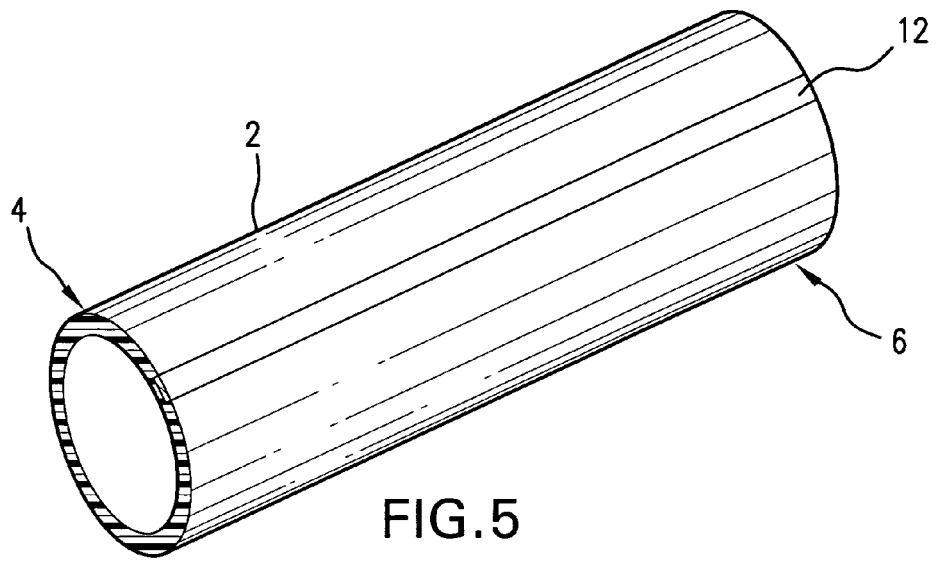
FIG. 5 is a perspective view of the polymer tube having a channel with a predetermined pattern.
Figure 6:
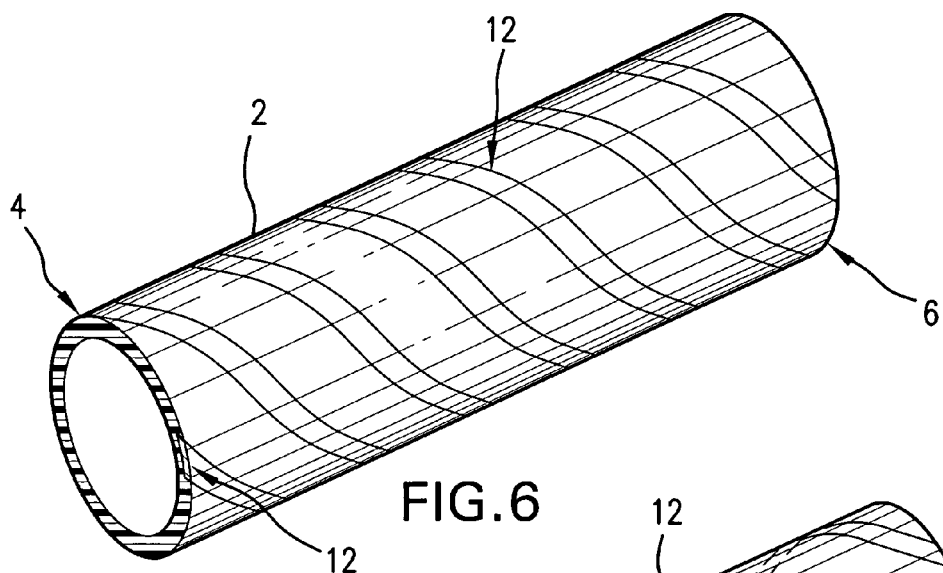
FIG. 6 is another perspective view of an exemplary embodiment of the polymer tube having a channel with a predetermined pattern.
Figure 7:
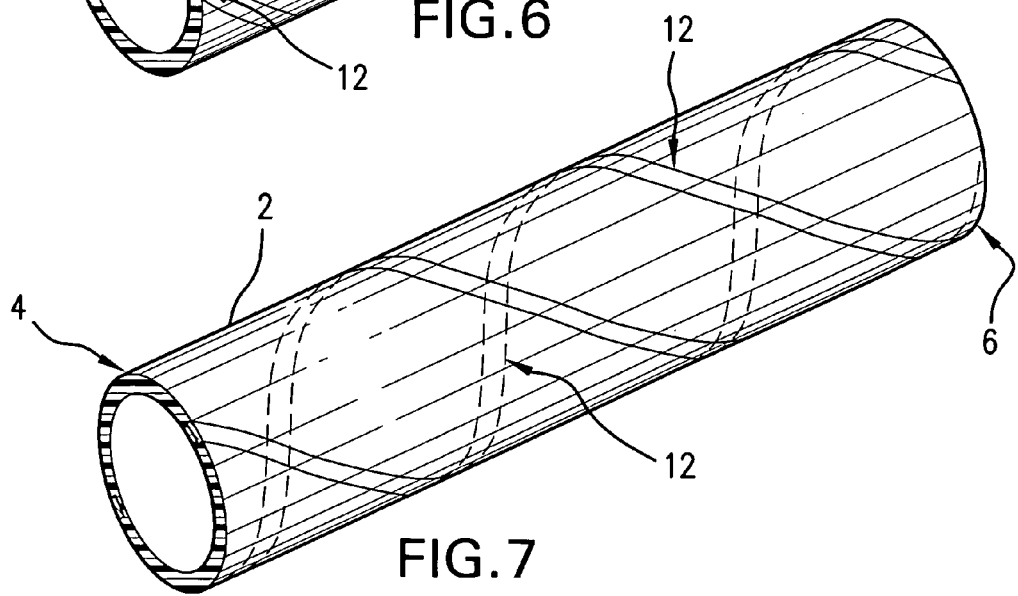
FIG. 7 is yet another perspective view of another exemplary embodiment of the polymer tube having a channel with a predetermined pattern.

As shown in FIGS. 5-7, the focused energy beam 16 creates at least one channel 12 having a predetermined pattern within the polymer tube 2. The predetermined pattern formed on the polymer tube 2 may be of any type desired to ensure the conduction of an electrical signal the length of the polymer tube 2. As detailed above, since the polymer tube 2 is adapted to be coupled to electrical devices, the channel 12 having a predetermined pattern will carry electrical signals/power from the proximal end 4 to the distal end 6 and vice versa.

The predetermined patterns that are formed on the polymer tube extend in an axial direction from a proximal end 4 to a distal end 6 of the polymer tube 2. The channel 12 with the predetermined pattern may extend the entire length in the axial direction of the polymer tube 2 or any portion necessary to enable coupling to an electrical device. In a preferred embodiment as shown in FIG. 5, the channel 12 having a predetermined pattern will extend in axial direction 20 from the proximal end 4 to the distal end 6 of the polymer tube 2 in a linear pattern. In this manner, the pattern will extend lengthwise in the axial direction on the polymer tube 2 and thus the electrical signal will be carried in the axial direction through the linear predetermined pattern on the channel 12. In exemplary embodiments as shown in FIGS. 6 and 7, the channel 12 having a predetermined pattern extends from the proximal end 4 to the distal end 6 of the polymer tube 2 in a helical or spiral pattern.

The predetermined pattern chosen for the channel 12 may be of any type suitable to enhance carrying of electrical signals and coupling of electrical devices to the polymer tube 2, such as a catheter, and is not limited to the embodiments shown in the Figures. An example as detailed above, the polymer tube 2, such as a catheter, may be coupled to a video camera. In this manner, the channel 12 with a predetermined pattern (for example, linear, spiral or helical) will extend from a proximal end 4 to a distal end 6 of the polymer tube 2 such that the video camera may be attached at either the proximal end 4 or distal end 6 for use in medical procedures within the human body.

The depth and shape of the ablated channel 12 having a predetermined pattern is defined by controlling the number of pulses, as well as the pulse rate, delivered to each illuminated region as the focused energy beam 16 is scanned over the polymer tube 2. With computer control, as detailed above, control over all aspects of the focused energy beam 16 and the displaceable and rotatable mounting is maintained which ensures proper ablation of the channel(s) 12 having a predetermined pattern.

Following the formation of at least one channel 12 having a predetermined pattern in the polymer tube 2, the polymer tube 2 is cleaned in order to remove any residue or debris left over from the ablation and vaporization of the polymer tube 2. The cleaning of the laser ablation debris from the polymer tube 2 may be performed by sonication in a liquid. Where cleaning is performed by sonication in a liquid, the cleaning process is followed by drying the polymer tube 2 in an oven to remove the remaining liquid.

Referring to FIG. 2, the channel 12 with a predetermined pattern is then filled with a low-temperature electrically conductive paste or electrically conductive slurry material 18. One such suitable material is PARMOD® PRA-311 silver paste, made by Parelec, Inc. of Rocky Hill, N.J. PARMOD® silver pastes and inks are disclosed in U.S. Pat. Nos. 5,882, 722; 6,036,889; 6,143,356; and 6,379,745.

The material used to fill the channel 12 having a predetermined pattern is an electrically conductive paste or electrically conductive slurry material 18. The electrically conductive paste or electrically conductive slurry material 18, in the preferred embodiment, is formed of metallic particles and metallic precursor compounds specifically silver particles and silver precursor compounds. In the preferred embodiment, the metallic particles, such as the silver particles, each having an average diameter of 5 micrometers and the metallic precursor compounds, such as the silver precursor compounds, are chosen to include materials which convert to solid-phase electrically conductive materials at temperatures less than 250° C. Further, the conductive material may include liquid solvents. The liquid solvents may, preferably, include dipropylene glycol methyl ether added at 1.1 weight percentage. Additionally, the conductive material may include compounds promoting adhesion of the solid-phase electrically conductive materials to the polymer tube 2. These solid-phase electrically conductive materials are produced in the final heating stage of the polymer tube 2, which converts the conductive paste to a solid-phase electrically conductive material, and the adhesion-promoting compounds may be, for example, diamines; or propylene glycol ethers.

Filling techniques for the electrically conductive paste or electrically conductive slurry material 18 can incorporate, but are not limited to, use of a squeegee device 8 adapted to cylindrical geometry (such as that of a polymer tube 2, for example, a catheter) such as that shown in FIG. 2. In this approach, electrically conductive paste or electrically conductive slurry material 18 is applied to the entire exterior of the polymer tube 2 and then selectively removed from the smooth outer wall surfaces by passing the polymer tube 2 through a flexible orifice. After filling of the channels 12 having a predetermined pattern, the polymer tube 2 is baked at a temperature sufficient to cure the electrically conductive paste or electrically conductive slurry material 18 (as will be detailed in the following paragraphs), but below that which will melt or soften the polymer tube 2.

FIG. 2 also illustrates the application of the electrically conductive paste or electrically conductive slurry material 18 to the polymer tube 2 and filling of channel 12 to form a predetermined pattern with the electrically conductive paste or electrically conductive slurry material 18. Following the application of the electrically conductive paste or electrically conductive slurry material 18, the polymer tube 2 and the electrically conductive paste or electrically conductive slurry material 18 are heated to a temperature of less than 250° C. in order to cure the electrically conductive paste or electrically conductive slurry material 18. This results in the channel 12 having predetermined patterns filled with electrically conductive paste or electrically conductive slurry material 18. If the channel 12 having the predetermined pattern is filled with a silver conductive paste material, such will include silver flake and silver necadecanoate in neodecanoic acid with a 6 to 1 ratio of silver flake to silver neodecanoate.

The heating and curing of the electrically conductive paste or electrically conductive slurry material 18 acts to not only cure the material, but shape the electrically conductive paste or electrically conductive slurry material 18, increase the material's strength and remove impurities from the electrically conductive paste or electrically conductive slurry material 18. The polymer tube 2 and the electrically conductive paste or electrically conductive slurry material 18 are heated to a temperature of less than 250° C., in the preferred embodiment, in order to convert the electrically conductive paste or electrically conductive slurry material 18 to solid-phase electrically conductive material.

During the thermal cure cycle, the electrically conductive paste or electrically conductive slurry material 18 may exhibit shrinkage, such that the cured material no longer completely fills the channels 12 having a predetermined pattern. Additional applications of electrically conductive paste or electrically conductive slurry material 18 followed by thermal curing may be necessary to achieve complete filling of the channels 12 with the electrically conductive paste or electrically conductive slurry material 18.

Referring again to FIG. 2, after additional applications, excess conductive fill material (the electrically conductive paste or electrically conductive slurry material 18) is removed again from the surface of the polymer tube 2, for example by the squeegee technique detailed above. After removal of excess electrically conductive paste or electrically conductive slurry material 18, the polymer tube 2 is heated, once again, to temperatures of less than 250° C. in order to convert the additional application of electrically conductive paste or electrically conductive slurry material 18 into a solid-phase electrically conductive material.

Figure 4:
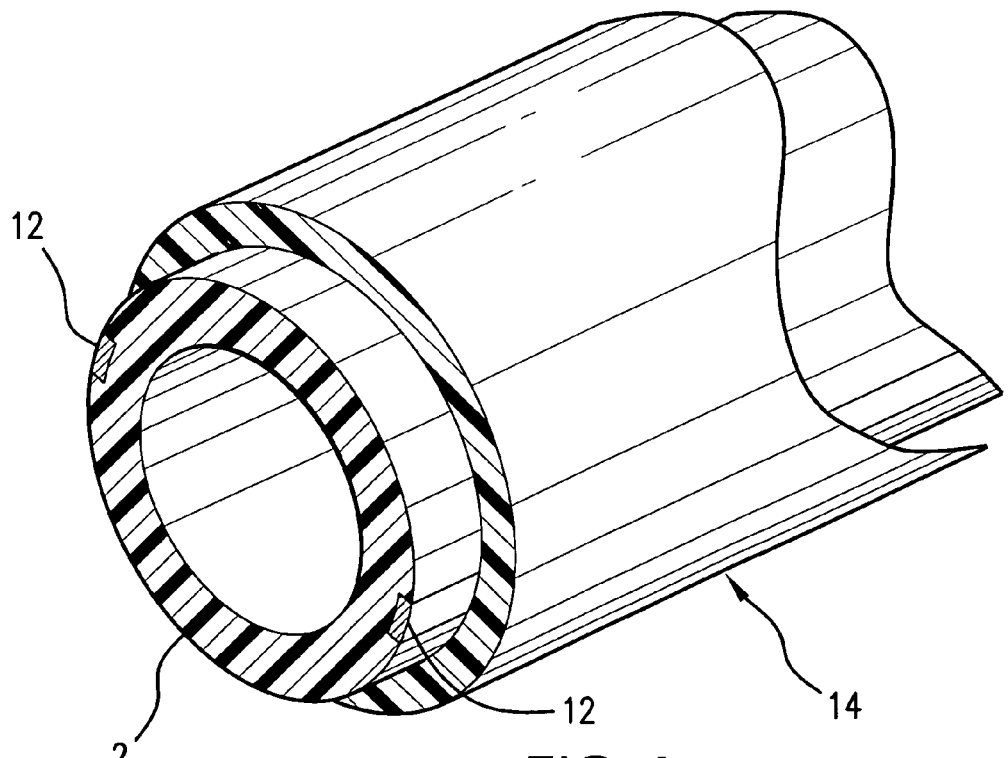
FIG. 4 is a perspective view of the biologically compatible polymer layer covering the polymer tube.

Referring to FIG. 4, once the polymer tube 2 with the electrically conductive paste or electrically conductive slurry material 18 is heated to cure the electrically conductive paste or electrically conductive slurry material 18, the electrically conductive paste or electrically conductive slurry material 18 is covered with a polymer layer 14. In a preferred embodiment, the polymer layer 14 will be a biologically compatible polymer layer 14 such that once the polymer tube 2 is placed within the human body, the electrically conductive paste or electrically conductive slurry material 18 will be protected from any fluids or external factors by the biologically compatible polymer layer 14 and vice versa. Furthermore, the biologically compatible polymer layer 14 will serve to firmly anchor the electrically conductive paste or electrically slurry material 18 in the channel 12 having the predetermined pattern as well as providing a protective interface between the electrically conductive paste or electrically conductive slurry material 18 and the surrounding biological environment (such as polymer tube 2, such as a catheter, being placed within the body during a medical procedure).

In one embodiment, all or a section of the patterned polymer tube 2 can be placed inside of a larger tube (polymer layer 14) fabricated from a heat-shrinkable material such as PTFE (polytetrafluoroethylene). The heat-shrink tubing is then thermally processed at temperatures compatible with the polymer tube 2 thereby producing a protective sleeve in intimate contact with the polymer tube 2.

In an exemplary embodiment, the polymer tube with the channels 12 having a predetermined pattern filled with the electrically conductive paste or electrically conductive slurry material 18 will be passed through a polymer extrusion device which applies a thin layer of molten polymer 14 over all or a portion of the catheter tube and the filled channel 12. The geometry and composition of the polymer layer 14 extruded on the polymer tube 2 can be chosen to provide biochemical and mechanical characteristics that are compatible with the application of interest (such as use in medical procedures).

Figure 3:
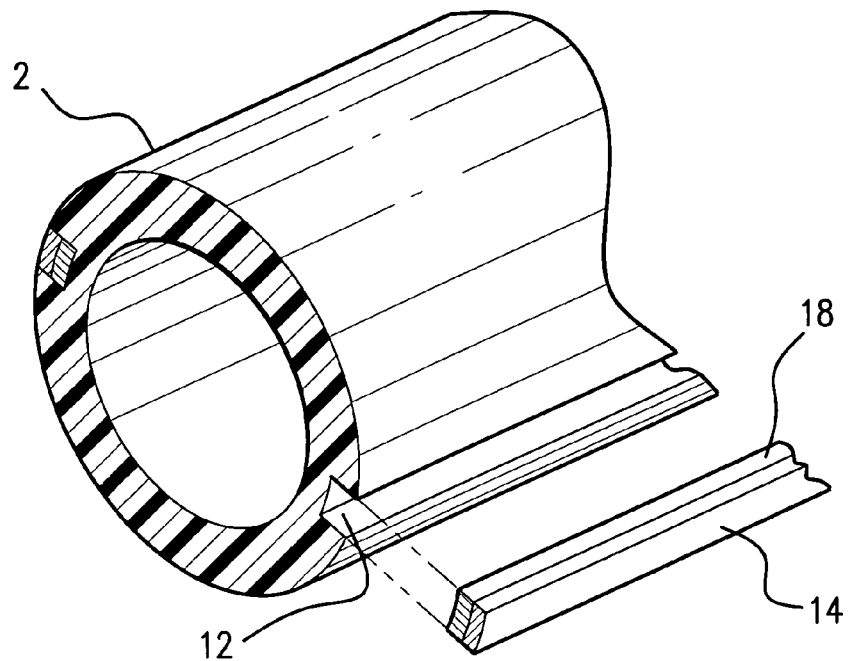
FIG. 3 an exploded view of the channels having a predetermined pattern.

In yet another exemplary embodiment, as shown in FIG. 3, an electrically conductive paste or electrically conductive slurry material 18 is utilized which exhibits significant shrinkage during thermal curing, thus resulting in a partially filled channel 12 having the predetermined pattern. A second fill cycle, is then used to fill the remainder of the channel 12 having a predetermined pattern, with an appropriate polymer material (such as a biologically compatible polymer material 14) which cures with minimal shrinkage and good adhesion to the channel 12 walls to effectively seal the outer portion of the channels and isolate the electrically conductive paste or electrically conductive slurry material 18 from the ambient environment. Such a type of filled channel 12 in a polymer tube 2 is shown in FIG. 3.

FIGS. 5-7 illustrate completed polymer tube 2 with channel(s) 12 having various predetermined patterns including the electrically conductive paste or electrically conductive slurry material 18. The predetermined patterns of the channel 12 shown as linear, helical or spiral are not limited to such predetermined patterns and may incorporate any predetermined pattern to enhance coupling to electrical devices.

Although this invention has been described in connection with specific forms and embodiments thereof, it will be appreciated that various modifications other than those discussed above may be resorted to without departing from the spirit or scope of the invention. For example, functionally equivalent elements may be substituted for those specifically shown and described, proportional quantities of the elements shown and described may be varied, and in the formation method steps described, particular steps may be reversed or interposed, all without departing from the spirit or scope of the invention as defined in the appended Claims.

What is claimed is:

1. A method for forming electrically conductive patterns to provide an electrically conductive path on polymer tubing comprising the steps of:
   (a) establishing a polymer tube having an axis defining an axial direction;
   (b) mounting said polymer tube in a displaceable and rotatable mounting adapted to provide both axial and rotational motion;
   (c) forming at least one channel having a predetermined pattern in said polymer tube with a focused energy beam;
   (d) filling said at least one channel having a predetermined pattern with an electrically conductive paste or electrically conductive slurry material, said electrically conductive paste or electrically conductive slurry material being formed of conductive particles and precursor compounds which convert to solid-phase electrically conductive compositions at temperatures of less than 250° C.;
   (e) heating said polymer tubing to temperatures less than 250° C. to cure said electrically conductive paste or electrically conductive slurry material; and,
   (f) covering said electrically conductive paste or electrically slurry material with a polymer layer.

2. The method for forming electrically conductive patterns to provide an electrically conductive path on polymer tubing as recited in claim 1, wherein said conductive particles each have an average diameter of less than or equal to five micrometers.

3. The method for forming electrically conductive patterns to provide an electrically conductive path on polymer tubing as recited in claim 1, wherein said electrically conductive patterns are formed of radio-opaque materials.

4. The method for forming electrically conductive patterns to provide an electrically conductive path on polymer tubing as recited in claim 1, wherein said focused energy beam is generated by a frequency-converted solid state laser.

5. The method for forming electrically conductive patterns to provide an electrically conductive path on polymer tubing as recited in claim 1, wherein the step of forming at least one channel having a predetermined pattern further includes the step of cleaning said polymer tubing to remove residue from said polymer tubing.

6. The method for forming electrically conductive patterns to provide an electrically conductive path on polymer tubing as recited in claim 1, wherein said electrically conductive paste or electrically conductive slurry material further includes compounds promoting adhesion of said solid phase conductive material to said polymer tubing.

7. The method of forming electrically conductive patterns to provide an electrically conductive path on polymer tubing as recited in claim 6, wherein said adhesion-promoting compounds are diamines.

8. The method of forming electrically conductive patterns to provide an electrically conductive path on polymer as recited in claim 1, wherein said polymer layer is a biologically compatible polymer layer.

9. The method of forming electrically conductive patterns to provide an electrically conductive path on polymer tubing as recited in claim 1, wherein the step of covering said electrically conductive paste or electrically conductive slurry material includes the step of covering an exterior surface of said polymer tubing with said polymer layer.

10. The method of forming electrically conductive patterns to provide an electrically conductive path on polymer tubing as recited in claim 9, wherein the step of covering an exterior surface of said polymer tubing with said polymer layer includes the step of extruding said polymer layer on said exterior surface of said polymer tube.

11. The method of forming electrically conductive patterns to provide an electrically conductive path on polymer tubing as recited in claim 9, wherein the step of covering said exterior surface of said polymer tube with said polymer layer includes the step of heat shrinking said polymer layer on said exterior surface of said polymer tube.

12. The method of forming electrically conductive patterns to provide an electrically conductive path on polymer tubing as recited in claim 1, wherein the step of filling at least one channel having a predetermined pattern includes the step of partially filling said at least one channel with a first layer of said electrically conductive paste or electrically conductive slurry material and forming a second layer of polymer contiguously with said first layer of electrically conductive paste or electrically conductive slurry material.

13. The method of forming electrically conductive patterns to provide an electrically conductive path on polymer tubing as recited in claim 1, wherein said at least one channel having a predetermined pattern extends in said axial direction from a distal end to a proximal end of said polymer tube.

* * * * *